(12) United States Patent
Evans et al.

(10) Patent No.: US 7,809,765 B2
(45) Date of Patent: Oct. 5, 2010

(54) SEQUENCE IDENTIFICATION AND ANALYSIS

(75) Inventors: Scott Charles Evans, Schenectady, NY (US); Thomas Stephen Markham, Schenectady, NY (US); Andrew Soliz Torres, Troy, NY (US)

(73) Assignee: General Electric Company, Niskayuna, NY (US)

( * ) Notice: Subject to any disclaimer, the term of this patent is extended or adjusted under 35 U.S.C. 154(b) by 622 days.

(21) Appl. No.: 11/844,619

(22) Filed: Aug. 24, 2007

(65) Prior Publication Data

US 2009/0055425 A1 Feb. 26, 2009

(51) Int. Cl.
*G06F 17/30* (2006.01)
(52) U.S. Cl. .................. 707/802; 707/803; 707/804
(58) Field of Classification Search ........... 707/802, 707/803, 804; 435/331, 333
See application file for complete search history.

(56) References Cited

U.S. PATENT DOCUMENTS

| | | | |
|---|---|---|---|
| 5,136,686 A | | 8/1992 | Koza |
| 5,455,577 A * | | 10/1995 | Slivka et al. .................. 341/51 |
| 5,617,552 A * | | 4/1997 | Garber et al. .................. 711/1 |
| 5,703,581 A * | | 12/1997 | Matias et al. ................. 341/67 |
| 6,373,971 B1 | | 4/2002 | Rigoutsos et al. |
| 6,473,757 B1 | | 10/2002 | Garofalakis |
| 7,043,371 B2 | | 5/2006 | Wheeler |
| 2002/0183936 A1 * | | 12/2002 | Kulp et al. .................... 702/19 |
| 2003/0207312 A1 * | | 11/2003 | Sorge ........................... 435/6 |
| 2004/0010504 A1 * | | 1/2004 | Hinrichs et al. ............. 707/100 |
| 2004/0249574 A1 | | 12/2004 | Tishby |
| 2005/0227243 A1 * | | 10/2005 | Deak et al. ...................... 435/6 |
| 2005/0273274 A1 | | 12/2005 | Evans |
| 2006/0246490 A1 * | | 11/2006 | Anderson et al. ............... 435/6 |
| 2007/0180151 A1 * | | 8/2007 | Richardson et al. ......... 709/248 |
| 2008/0005547 A1 * | | 1/2008 | Papakipos et al. ........... 712/244 |
| 2008/0205280 A1 * | | 8/2008 | Saphir ......................... 370/236 |
| 2009/0216521 A1 * | | 8/2009 | Swoboda et al. .............. 703/26 |

OTHER PUBLICATIONS

Moses Charikar et al., "Approximating the Smallest Grammar: Kolmogorov Complexity in Natural Models", Proceedings of Annual ACM Symposium, Feb. 20, 2002, pp. 792-801.
S.C. Evans and S.F. Bush, "Symbol Compression Ratio for String Compression and Estimation of Kolmogorov Complexity", Nov. 2001, 16 Pages.
Craig G. Nevill-Manning and Ian H. Witten, "On-Line and Off-Line Heuristics for Inferring Hierarchies of Repetitions in Sequences", Proceedings of the IEEE, vol. 88, No. 11, Nov. 2000, pp. 1745-1755.

(Continued)

*Primary Examiner*—Wilson Lee
*Assistant Examiner*—Hanh B Thai
(74) *Attorney, Agent, or Firm*—Fletcher Yoder

(57) ABSTRACT

The present technique provides for the analysis of a data series to identify sequences of interest within the series. Specifically, in accordance with one embodiment of the present technique, a method is provided comprising generating a data structure that stores characteristics about a plurality of sequences present in a data series. One or more sequences are identified based upon the contents of the data structure. In accordance with other aspects of the invention, more than one heuristic is calculated for each sequence under review. The plurality of heuristics associated with each sequence are evaluated to identify a sequence of interest.

30 Claims, 4 Drawing Sheets

OTHER PUBLICATIONS

Alberto Apostolico and Stefano Lonardi, "Off-Line Compression by Greedy Textual Substitution", Proceedings of the IEEE, vol. 88, No. 11, Nov. 2000, pp. 1733-1744.

Scott C. Evans et al., "microRNA Target Detection and Analysis for Genes Related to Breast Cancer Using MDLcompress"; www.hindawi.com/journals/bsb/raa.43670.html.

S.C. Evans et al., "An Improved Minimum Description Length Learning Algorithm for Nucleotide Sequence Analysis", Proceedings of IEEE 40$^{th}$ Asilomar Conference on Signals, Systems and Computers, Pacific Grove, CA, Nov. 2006.

A. Apostolico et al., "Off-line Compression by Greedy Textual Substitution", Proc. IEEE, 88(11): 1733-1744.

O. G. Troyanskaya et al.; Title: "Sequence Complexity Profiles of Prokaryotic Genome Sequences: A fast Algorithm for Calculating Linguistic Complexity"; Bioinformatics; vol. 18 No. 5 2002; pp. 679-688.

Scott C. Evans; Title: "Kolmogorov Complexity Estimation and Application for Information System Security"; Rensselaer Polytechnic Institute; Troy, New York; Jul. 2003.

\* cited by examiner

```
                         SEQUENCE LISTING

<160> NUMBER OF SEQ ID NOS: 1

<210> SEQ ID NO 1
<211> LENGTH: 10
<212> TYPE: DNA
<213> ORGANISM: Homo sapiens

<400> SEQUENCE: 1
agcacttatt                                                        10
```

SEQUENCE IDENTIFICATION AND ANALYSIS

STATEMENT REGARDING FEDERALLY SPONSORED RESEARCH & DEVELOPMENT

This invention was made with Government support under contract number W81XWH-0-1-0501 awarded by U.S. Army Medical Research Acquisition Activity, 820 Chandler Street, Fort Detrick, DM 217-5014. The Government has certain rights in the invention.

REFERENCE TO SEQUENCE LISTING SUBMITTED ELECTRONICALLY

The present application contains a Sequence Listing of SEQ ID NO 1 in file "215720-1 Sequence Listing_ST25.txt" (380 bytes), created on Jul. 31, 2007, concurrently submitted with the specification by electronic filing, which is herein incorporated by reference in its entirety.

BACKGROUND

The invention relates generally to data analysis and, more specifically, to the identification of sequences within a data series.

In various applications, such as information theory, data compression, and intrusion detection, it may be desirable to identify sequences of interest, within a larger data series. It may be advantageous to identify such sequences of interest to extract meaningful information from the identified sequences or to allow for manipulation or analysis of the data series. For example, identification of repetitive sequences in a data series may allow for effective compression of the data or may indicate sequences having particular significance.

In the field of genetics, biologically significant sequences in a DNA strand tend to have higher redundancy than non-meaningful sequences. For the genomes, which are known or are being sequenced, the purposes of different parts of the genomes are currently unknown. Additionally, the identification of meaningful or interesting sequences within a genome poses a challenge. Hence, it may be desirable to develop techniques that efficiently and accurately recognize sequences of interest within a larger data series.

BRIEF DESCRIPTION

Briefly, in accordance with one aspect of the present technique, a method is provided for identifying a candidate sequence of interest. A given data series and initial grammar are provided, from which a data structure is generated. This data structure stores characteristics about potential candidate sequences, upon which identification of the candidate sequence will depend. Upon identification of a sequence based upon the sequence characteristics, one or more exit criteria (such as a determination of whether the identified sequence provides greater than a threshold amount of compression or whether a desired number of iterations have been performed) are evaluated to determine if an exit point has been reached. If the exit criteria are not met, the data structure is updated to reflect the most recent identification of a candidate sequence and the identification process is repeated. If the exit criteria are met, the process is terminated.

In accordance with another aspect of the present technique, each candidate sequence identified in the data series is evaluated in view of multiple heuristics, such as the symbol compression ratio, the longest match, and the total compression heuristics described below. The evaluation may be performed for a single iteration or may include subsequent iterations. Based on this evaluation of multiple heuristic measures, a candidate sequence is identified. Upon identification of a candidate sequence, one or more exit criteria are evaluated to determine if an exit point has been reached or if the process is to proceed through another iteration.

In one aspect of the present technique, a method is provided for identifying a sequence of interest in a data series. The method includes the step of generating a data structure that stores characteristics about a plurality of sequences present in the data series. One or more sequences are identified based upon the contents of the data structure. One or more exit criteria (such as comparing the compression associated with the candidate sequence with a threshold, comparing the number of iterations performed with a desired number of iterations, and so forth) are evaluated to determine if an exit point has been reached. If the exit criterion or criteria are not met, the data structure is updated to reflect the most recent identification of a sequence and the identification process is repeated. If the exit criteria are met, the process is terminated. Tangible, machine-readable media is provided, comprising code adapted to perform the method described immediately above.

In another aspect of the present technique, a method for identifying a sequence of interest is provided. The method includes the act of evaluating a plurality of heuristics (such as the symbol compression ratio heuristic, the total compression heuristic, the longest match heuristic discussed herein) for a candidate sequence from a plurality of candidate sequences present in a data series. A sequence in the plurality of candidate sequences is identified based on the evaluation of the heuristics. One or more exit criteria are evaluated to determine if an exit point has been reached. If no exit criteria are met, the data series, or a corresponding data structure, is updated to reflect the most recent identification of a sequence and the identification process is repeated. If one or more of the exit criteria are met, the process is terminated. Corresponding code provided on one or more tangible, machine-readable media is also provided.

In yet another aspect of the present technique, a method is provided for identifying a biological sequence of interest. The method includes the act of generating a data structure that stores characteristics about potential biological sequences of interest present in a biological polymer. One or more biological sequences are identified based upon the contents of the data structure. One or more exit criteria are evaluated to determine if an exit point has been reached. If the exit criteria are not met, the data structure is updated to reflect the most recent identification of a biological sequence and the identification process is repeated. If the exit criteria are met, the process is terminated.

DRAWINGS

These and other features, aspects, and advantages of the present invention will become better understood when the following detailed description is read with reference to the accompanying drawings in which like characters represent like parts throughout the figures, wherein.

DETAILED DESCRIPTION

In many fields, such as genomic sequencing and analysis, it may be desirable to identify repetitive sequences of interest in a data series, either to assist in compression and manipulation of the data or to facilitate analysis. Further, it may be desirable to identify such sequences in a computationally efficient manner. With this in mind, the execution of the present technique may be divided into two parts: (1) an initial statistics gathering phase, and (2) an iterative sequence identification phase using the statistics. The techniques described herein further address these issues.

Figure 1:
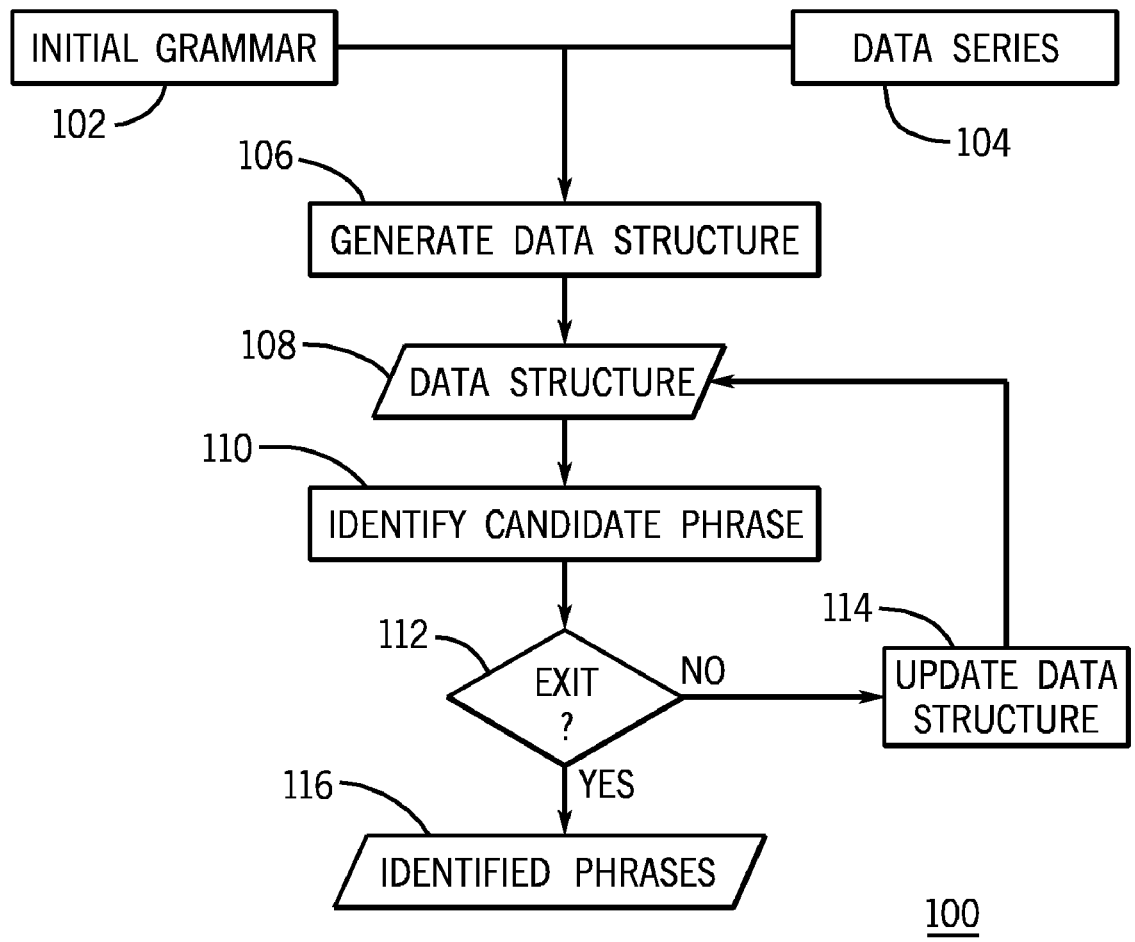
FIG. 1 is a flowchart depicting steps for identifying a sequence of interest in a data series, in accordance with one aspect of the present technique.

Turning now to FIG. 1, a flowchart is depicted which describes acts for identifying a sequence of interest from a data series, in accordance with one aspect of the present technique. The flowchart is generally referred to by the reference number 100. As indicated by the flowchart 100, a given data series 104 may be provided, within which may be one or more sequences of interest to be identified. The data series 104 may be described or expressed in terms of an initial grammar 102. The initial grammar 102 generally defines the characters or symbols, either alone or in combination, which may be found within the data series 104. The initial grammar 102 may comprise terminals (uncombined symbols) and/or variables (combinations of terminals or combinations of terminals and variables). When the data series is numerical, the grammar may include the numerals 0-9 as terminals and/or may include combinations of the terminals (e.g., 10, 22, 360) as variables. Similarly, an alphanumeric data series 12 may include numerals 0-9, the alphabetic letters, punctuation marks, and so forth as terminals and combinations of the terminals as variables. In the context of biological sequences, such as deoxyribonucleic acid (DNA) sequences and ribonucleic acid (RNA) sequences or peptide sequences, the grammar 102 may include symbols representing nucleotides or amino acids, respectively.

In embodiment in shown FIG. 1, a data structure 108 is generated (Block 106) based on the initial grammar 102 and the data series 104. In one implementation, the data structure 108 includes a matrix storing locations of each sequence within the data series 104 and an array in which characteristics of each sequence are stored. In a computerized or other automated implementation of the present technique, memory usage and runtime may be improved by using the data structure 108 to store information about each candidate sequence within the initial data series 104, to calculate and/or store the relevant descriptors or characteristics for each sequence, and to update the data structure 108 for all remaining candidate sequences when a candidate sequences is identified, as described in more detail below. Thus, in such an implementation, operations are performed on the data structure 108, once generated, as opposed to on the data series itself. In an exemplary embodiment where sequence identification is based upon a compression criterion, compression is evaluated based upon the global structure of the data series 104 rather than being based upon which sequences are processed first.

Once the data structure 108 is generated, one or more candidate sequence may be identified (Block 110) based on the contents of the data structure. In the depicted implementation, upon identification of a candidate sequence one or more exit criteria are evaluated (Block 112) to determine if an exit point in the process has been reached. For example, in some embodiments, the exit criteria may relate to the relative or absolute amount of compression provided by the presently identified candidate sequence or whether that amount of compression exceeds a designated threshold value. Likewise, in other embodiments, the exit criteria may relate to a number of iterations performed, which may or may not be weighted by the amount of compression being obtained in the present iteration. If the exit criteria are not met, the data structure 108 is updated (Block 114), as described above, to reflect the most recent identification of a candidate sequence and the identification process is repeated. Conversely, if the exit criteria are met, the identified candidate sequences 116 are provided for further analysis.

The various acts described herein, such as those described with reference to FIG. 1 as well as those described below, may be performed by a computer or other processor-based system executing code or routines corresponding to the described acts. Such code or routines may be provided on suitable media, such as magnetic or optical media, that may be provided as part of the computer, such as on a hard disk drive or drives, or on removable media, such as on an optically read disk or disks or a removable memory device. In such implementations, one or more processors of the computer typically execute the code or routines stored on the media. Various memory components of the computer provide temporary storage of code to be executed by the processor(s) and/or of output generated by the executed code. Typically a monitor or other output device, such as a printer, may be used to provide identified output to an operator.

Figure 2:
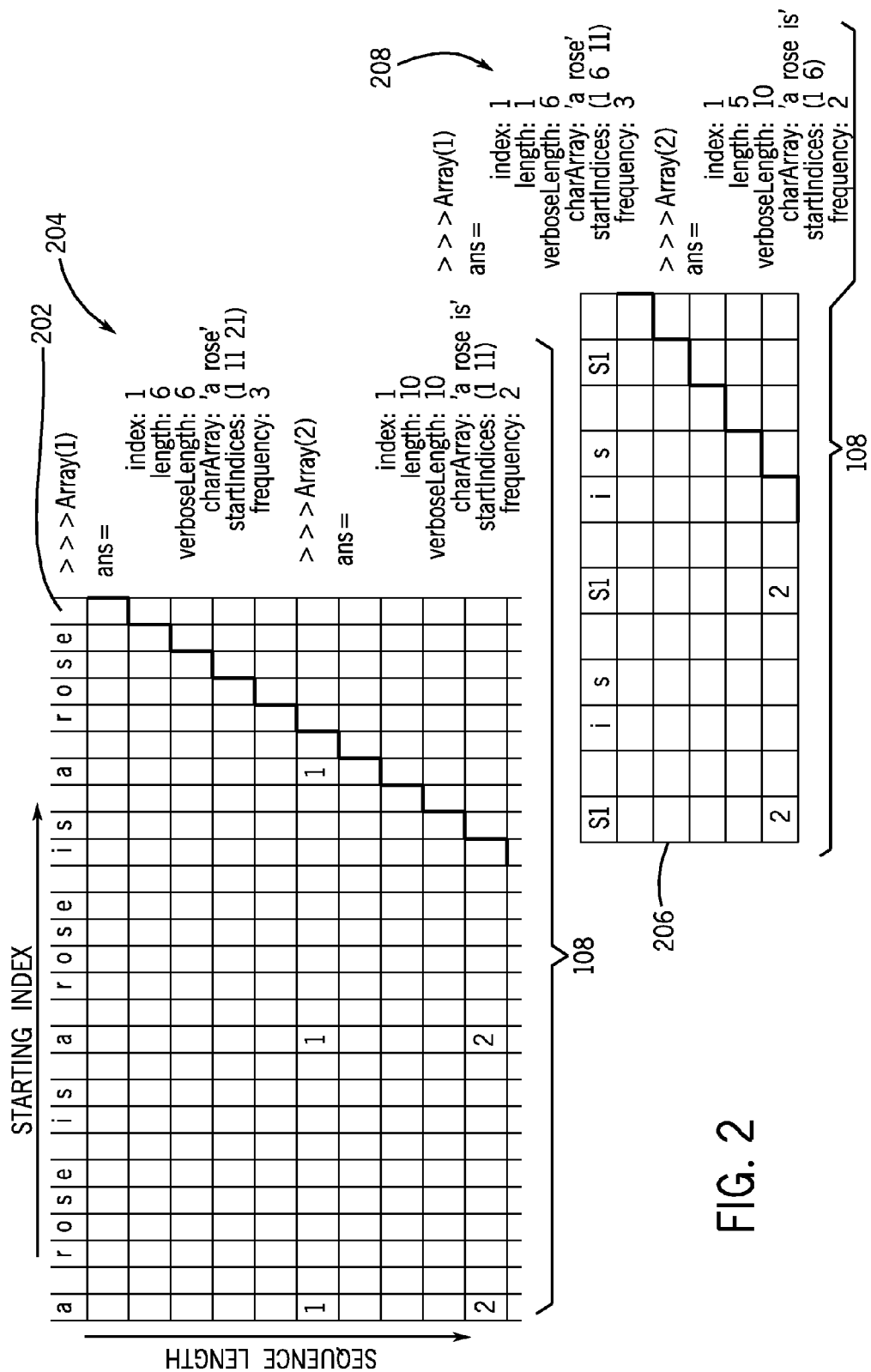
FIG. 2 is an illustration of the formation and maintenance of matrix structures, in accordance with one aspect of the present technique.

Turning now to FIG. 2, a data structure 108 in the form of a matrix 202 and corresponding array 204 is provided. In the depicted example, the data structure 108 stores statistics or other characteristics about potential candidate sequences, in a data series 104. In one implementation, the data structure 108 is one or more simple matrix structures that store information on sequence frequencies and relationships between sequences, such as spatial relationships. While a two-dimensional matrix is depicted, higher dimensional matrices, such as three- or four-dimensional matrices, may also be employed. Further, in an exemplary embodiment, the one or more matrix structures 202 and/or arrays 204 may be initially generated in a single pass through the data series 104. In such embodiments, the matrix structures 202 and/or arrays 204 may be iteratively updated as sequence identification proceeds without further reference to the data series 104.

In one embodiment, during an initial analysis, of the data series 104, a $l_{max}$ by L matrix 202 is generated, where entry $M_{i,j}$ represents the candidate sequence of length i beginning at index j. In one embodiment, the matrix 202 is a sparse matrix, with entries only at locations that represent candidate sequences. Candidate sequences with no repeats and/or that only appear as part of a longer candidate sequence are represented with a 0 or by no entry. Matrix locations with positive entries represent an index into an array, e.g., array 204, storing additional details for the respective candidate sequence, such as details about sequence frequency, length, and/or any statistical heuristic values (symbol compression ratio heuristic, total compression heuristic, longest match heuristic, and so forth) calculated for the sequence.

In one embodiment, for candidate sequences with input length, L, and maximum length, $l_{max}$, the memory requirement of the initial analysis in which the data structure 108 is populated, is bounded by the product $L*l_{max}$. In implementations where the user may define a constraint on $l_{max}$, memory use may be restricted to as little as O(L), and will generally not exceed $O(L^2)$. This allows a user to adjust memory usage and/or analysis based on memory constraints. For example, on platforms with limited memory where long sequences are expected to exist in the data series 104, a longest match (LM) heuristic may be used in a simple pre-processing pass to identify and replace any sequences longer than the system can handle using the available matrix. Because the present technique inspects the data structure 108 when subsequently searching for candidate sequences, the technique has minimal negative effect on overall compression.

The runtime of the initial pass by which the data structure 108 is generated, generally depends on L, $l_{max}$, average sequence length $l_{avg}$, and average number of repeats of identified sequences, $r_{avg}$. In an exemplary implementation, the product $l_{avg}*r_{avg}$ is less than L and the maximum sequence length is less than $$\frac{L}{2},$$

to provide a performance boundary of $O(L^3)$. In one implementation, a memory constraint may limit $l_{max}$ to a constant independent of L, and $l_{avg}*r_{avg}$ may be approximately constant and smaller than L. Thus, the practical performance bound is $O(L)$ in such an implementation.

In example shown in FIG. 2, the data series 104 is "a_rose_is_a_rose_is_a_rose." In this data series 104, the sequence "a_rose" appears three times, as denoted in the frequency line of the corresponding array 204. The corresponding array 204 also includes the length of the sequence (six spaces) and the start indices (spaces 1, 11, and 21). The locations and start points of this sequence is indicated in the matrix 202 with a "1". Similarly, the sequence "a_rose_is" appears twice in the data series 104 and is so indicated in the corresponding frequency field of the array 204. The start points and locations of this second sequence are indicated by a "2" in the corresponding matrix 202 index boxes. As noted above, sequences that appear only as substrings of longer sequences need not be shown or indexed. For example, in the depicted matrix 202 and array 204, the sequence "a_ros" is not indexed as this sequence only appears as a substring in the sequence "a_rose".

In an exemplary embodiment, the array 204 of the data structure 108 is searched based on one or more heuristics that were calculated (or are calculated on the fly) for each entry. Once a candidate sequence is identified, the corresponding entries in the matrix 202 are used to pinpoint overlapping sequences, which will have their frequency reduced by the substitution of a new symbol in place of the identified sequence. While there may be many sequences in the array 204 that are updated, only limited sections of the matrix 202 are altered, thus, only a small percentage of the data structure 108 is updated. For example, based on such an iterative process, the data structure 108 may be revised, such as to generate updated matrix 206 and/or updated array 208, to reflect the substitution of a symbol, here S1, for the identified candidate sequence, here "a_rose". In such implementations, the present technique may be efficiently executed on lengthy data series 104, such as DNA, RNA or amino acid sequences.

Figure 3:
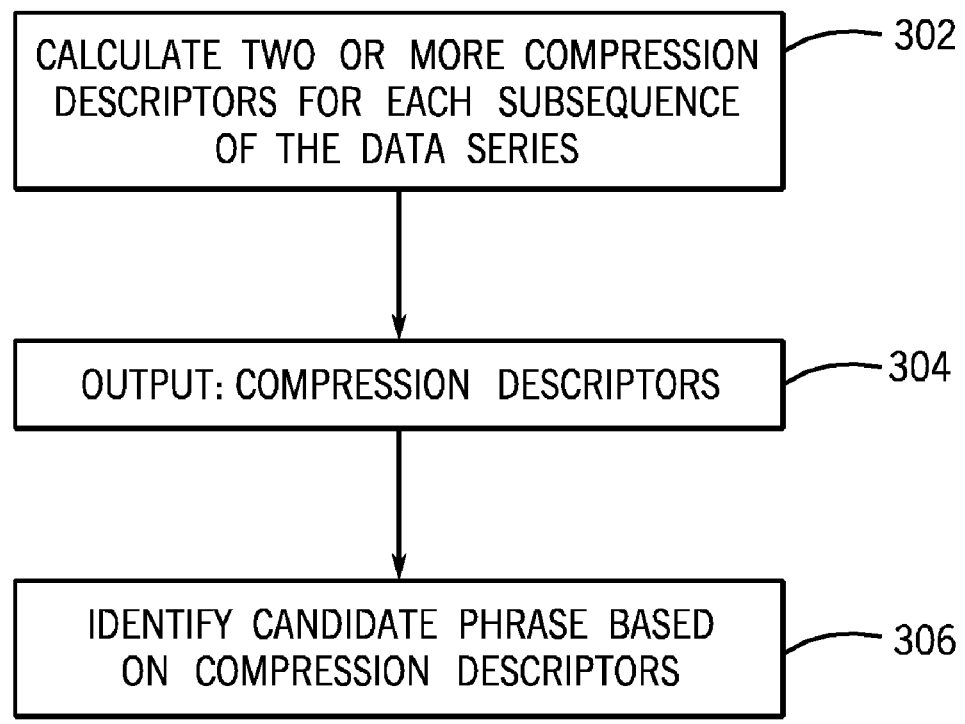
FIG. 3 depicts a method of identification of a candidate sequence of interest in accordance with one aspect of the present technique.

The preceding discussion describes the context and result of sequence identification. The mechanism of sequence identification is now discussed in greater detail. Referring to FIG. 3, exemplary acts for identifying a candidate sequence in accordance with one aspect of the present technique are depicted. In this example, two or more descriptors 304 are calculated (Block 302) for each candidate sequence referenced by the data structure 108. In an exemplary embodiment, the descriptors 304 may be calculated using different heuristics for each sequence in accordance with respective compression or other algorithms. Alternatively, in accordance with another exemplary embodiment, other descriptors might be calculated by way of different heuristic permutations. For example, compression might take place by sequential application of the same or different heuristics (e.g., Longest Match (LM), followed by Total Compression (TC)). In one implementation, the descriptors 304 are calculated in the initial analysis of the data series 104 and are stored with each respective candidate sequence in the data structure 108. The descriptors 304 for each sequence may be updated with each iteration of sequence identification. Based on the desired identification criteria, such as maximizing compression, a candidate sequence is identified (Block 306) during each iteration based on the respective descriptors 304 calculated for each sequence. In one implementation, the time in which identification and replacement of compressible sequences takes place is the sum of the time to identify a sequence and the time spent updating the data structure 108 for the next iteration multiplied by the number of iterations.

While the preceding describes the identification of a sequence using a descriptor (such as the value of a heuristic or permutations of the same or different heuristics), in some embodiments more than one sequence may be so identified. For example, in such embodiments, the top two or three scoring sequences may be identified as described above and processed separately through succeeding iterations. Indeed, each iteration may identify the top two or three results, thereby providing an extensive set of potential results for subsequent review. In this manner, at the conclusion of processing, a decision may be made, automatically or after operator review, as to which permutation of identified sequences provides the best result.

In an exemplary embodiment, some or all of the descriptors 304 may be calculated based upon Minimum Description Length (MDL) principles. MDL is related to Kolmogorov Complexity, a measure of descriptive complexity contained in an object. MDL refers to the minimum length l of a program such that a universal computer can generate a specific sequence. Kolmogorov Complexity may be described as follows, where φ represents a universal computer, p represents a program, and x represents a data series:

$$K_\varphi(x) = \left\{ \min_{\varphi(p)=x} l(p) \right\}. \tag{1}$$

An MDL decomposition of a binary data series x considering finite set models may be separated into two parts:

$$K_\phi(x) \stackrel{+}{=} \{K(S) + \log_2 |S|\} \tag{2}$$

where $K_\phi(x)$ is the Kolmogorov Complexity for data series x on universal computer φ. S represents a finite set of which x is a typical (equally likely) element. The minimum possible sum of descriptive cost for set S (the model cost encompassing all regularity in the data series) and the log of the sets cardinality (the cost to enumerate the equally likely set elements) corresponds to an MDL two part description for data series x, a model portion that describes all redundancy in the data series, and a data portion that uses the model to define the specific data series. Among all possible two-part descriptions of this date series the combination that minimizes the two-part descriptive cost is the MDL description.

By considering the model cost, as well as the data costs of a date series, MDL theory provides a formal methodology that justifies objectively classifying a data series. These concepts may be extended beyond the class of models that may be constructed using finite sets to all computable functions.

The size of the model (the number of bits allocated to spelling out the members of set S) is related to the Kolmogorov Structure Function, $\stackrel{+}{=}$. $\stackrel{+}{=}$ defines the smallest set, S, that can be described in at most k bits and contains a given data series x of length n:

$$\hbar_k(x^n \mid n) = \min_{p:l(p)<k, U(p,n)=S} \{\log_2 |S|\}. \quad (3)$$

This function has been interpreted as being a minimum sufficient statistic. The cardinality of the set containing data series x of length n starts out as equal to n when k=0 bits are used to describe set S. As k increases, the cardinality of the set containing data series x can be reduced until a critical value k* is reached which is referred to as the Kolmogorov Minimum Sufficient Statistic or Algorithmic Minimum Sufficient Statistic. At k*, the size of the two-part description of data series x equals $K_\varphi(x)$ within a constant. Increasing k beyond k* will continue to make possible a two-part code of size $K_\varphi(x)$, resulting in a description of a set containing the single element x. However, beyond k*, the increase in the descriptive cost of the model, while reducing the cardinality of the set to which x belongs, does not decrease the overall descriptive cost of the data series.

One exemplary embodiment of the present technique uses steepest-descent stochastic-gradient methods to infer grammar-based models based upon sequences that maximize compression. In such an embodiment, an algorithmic minimum sufficient statistic is estimated via a highly-recursive algorithm that identifies those motifs enabling maximal compression. In a further embodiment, the technique is performed recursively such that sequences are not removed from consideration for compression after they have been added to the grammar-based model.

An exemplary heuristic used to identify sequences in accordance with the present technique is the Symbol Compression Ratio (SCR). Examples of the derivation and use of SCR heuristics are disclosed in U.S. patent application Ser. No. 10/858,744, titled "Method for Identifying Sub-Sequences of Interest in a Sequence," filed on Jun. 2, 2004 to Evans et al., which is hereby incorporated by reference in its entirety. An exemplary SCR based technique is the Optimal Symbol Compression Ratio (OSCR) algorithm, which is a grammar inference algorithm that infers a two-part minimum description length code and an estimate of the Algorithmic Minimum Sufficient Statistic. OSCR produces meaningful models in an MDL sense, while achieving a combination of model components and data components whose descriptive size together estimate the Kolmogorov Complexity of the data set. OSCR's capability for capturing the regularity of a data set into compact, meaningful models has wide application for sequence analysis. The deep recursion of the new approach combined with its two-part coding nature makes an OSCR algorithm suitable for identifying meaningful sequences without limiting assumptions.

For example, in one embodiment, the entropy of a distribution of symbols defines the average per symbol compression bound in bits per symbol for a prefix free code. Huffman coding and other approaches may produce an instantaneous code approaching the entropy in the limit of infinite message length when the distribution is known. In the absence of knowledge of the model, one way to proceed is to measure the empirical entropy of the data series. However, empirical entropy is a function of the partition and depends on what sequences are grouped together to be considered symbols. In one implementation of the present technique, the partition (the number of symbols, their length, and distribution) of a data series is optimized such that the compression bound for an instantaneous code (the total number of encoded symbols R time entropy $H_s$) plus the grammar size is minimized. The approximate model descriptive cost M is defined to be the sum of the lengths of unique symbols, and total descriptive cost $D_p$ as follows:

$$M \equiv \sum_i l_i, \; D_p \equiv M + R \cdot H_s. \quad (4)$$

While not necessarily exact (for example, symbols delimiting "comma costs" may be ignored and/or possible redundancy advantages may not considered), these techniques provide an approximate means of breaking out MDL costs on a per symbol basis. Further, the following analysis may be adapted to other model cost assumptions.

For example, in seeking to partition the candidate sequence in one SCR implementation so as to minimize the total data series descriptive length $D_p$, the length that the presence of each symbol adds to the total descriptive length and the amount of coverage of total data series length L that it provides is considered. Since the probability of each symbol, $p_i$, is a function of the number of repetitions of each symbol, it may be easily shown that the empirical entropy for this distribution reduces to:

$$H_s = \log_2(R) - \frac{1}{R}\sum_i r_i \log_2(r_i). \quad (5)$$

Thus:

$$D_p = R\log_2(R) + \sum_i l_i - r_i \log_2(r_i), \text{ with} \quad (6)$$

$$R\log_2(R) = \sum_i r_i \log_2(R) = \log_2(\hat{R})\sum_i r_i \quad (7)$$

where $\log_2(\hat{R})$ is a constant for a given partition of symbols. Computing this estimate based on a current partition enables a per symbol formulation for $D_p$ and results in a conservative approximation for $R\log_2(R)$ over the likely range of R. The per-symbol descriptive cost may be formulated:

$$d_i = r_i[\log_2(\hat{R}) - \log_2(r_i)] + l_i. \quad (8)$$

Such an exemplary SCR heuristic conservatively estimates the descriptive cost of any possible symbol in a candidate sequence considering both model and data (entropy) costs. A measure of the compression ratio for a particular symbol is simply the descriptive length of the data series divided by the length of the data series "covered" by this symbol. Thus the Symbol Compression Ratio (SCR) is defined as:

$$\lambda_i = \frac{d_i}{L_i} = \frac{r_i \lfloor \log_2(\hat{R}) - \log_2(r_i) \rfloor + l_i}{l_i r_i}. \quad (9)$$

This heuristic describes the "compression work" a candidate symbol will perform in a possible partition of a data series. For example, good symbol compression ratios may generally arise when symbols are long and repeated often.

Thus, the Optimal Symbol Compression Ratio (OSCR) algorithm forms a partition of a data series 104 into symbols that have the best symbol compression ratio (SCR) among possible symbols contained in the data series 104. The algorithm starts with a grammar 102 that is used to form a list of candidate sequences, contained in a data series 104, possibly with user-defined constraints on minimum frequency and/or maximum length. The frequency of each candidate sequence is then noted. In one embodiment, the SCR is calculated for all candidate sequences and the candidate sequence from the current iteration is identified with the smallest SCR. The identified sequence is added to the model M. All occurrences of the newly added candidate sequence are replaced with a unique character. This process may be iterated until no suitable candidate sequences are found, until a set number of iterations have been performed, or until some other exit criteria have been met. When a full partition has been constructed, Huffman coding or another coding strategy may be used to encode the distribution, p, of the symbols.

This exemplary SCR algorithm progressively adds symbols that do the most compression "work" among all the candidates to the code space. Replacement of these symbols will alter the frequency of remaining symbols. Further, in some embodiments, a less exhaustive search for the optimal SCR candidate is possible by concentrating on the tree branches that dominate the data series or by searching only certain sequence lengths.

Considering the data series: "a_rose_is_a_rose_is_a_rose," with ASCII characters as the initial alphabet. In this example, the initial grammar includes the terminals {a, _, r, o, s, e, i} with respective initial frequencies of {3, 7, 3, 3, 5, 3, 2}. The candidate sequence "a_" has a length of 2, a frequency of 3 and an SCR of 1.023; the candidate sequence "a_rose" has a length of 6, a frequency of 3 and an SCR of 0.5; and the candidate phrase "a_rose_is_" has a length of 10, a frequency of 2 and an SCR of 0.7000. Thus the sequence "a_rose" has the closest SCR value, demonstrating that neither the longest nor the most frequent symbol will necessarily be chosen, but rather both frequency and length are weighted into the identification. A second iteration, after the sequence "a_rose" has been replaced with a symbol, such as $S_1$, results in the identification of the sequence "_is_$S_1$" such that, after two iterations, the initial data series may be represented as $S_1 S_2 S_2$. MDL principles may also be applied in this way as analogous to the problem of finding an optimal compression code for a given data set with the added constraint that the descriptive cost of the codebook must also be considered. Thus the cost of sending the result of prior iterations (a codebook or other modeling information) is considered in the total descriptive cost in addition to the descriptive cost of the final compressed data given the model.

In one embodiment of OSCR, computational complexity may be traded for space complexity to decrease execution time. Likewise, not only the data series 104 but also the grammar 102 may be searched for candidate sequences. Additional gains in compression may be achieved by taking into account sequence-specific features for which a priori information exists, such as palindromes, regions of local similarity, and single nucleotide polymorphisms (SNPs) in a biological implementation.

While the preceding discussion of SCR describes a general heuristic suitable for partitioning a sequence to provide the best compression, the approach may be enhanced to take into account additional effects. For example, adding new symbols to a partition increases the coding costs of other symbols by a small amount in the approach described above. Furthermore, for any given length and frequency, certain symbols ought to be preferred over others because of probability distribution effects.

In an exemplary implementation, the increase in coding costs and/or the preference toward certain symbols may be taken into account. Thus, costs may be separated into three parameters: (i) entropy costs, $C_h$ (costs to represent the new sequence in the encoded data series); (ii) previous costs, $C_p$ (costs to represent the sequence in the data series previously); and (iii) model costs, $C_m$ (costs to add the new sequence to the model). In accordance with this implementation, these costs may be broken down as follows:

$$C_h = R_i \cdot \log\left(\frac{\hat{R}}{R_i}\right) \quad (10)$$

where $\hat{R}$ is the length of the data series after substitution, $l_i$ is the length of the sequence, L is the length of the model, and $R_i$ is the frequency of the sequence in the data series.

For previous costs, the sum of the costs of the subsequences that comprise the candidate sequence are considered such that:

$$C_p = R_i \cdot \sum_{j=1}^{l_i} \log\left(\frac{\hat{R}'}{r_j}\right) \quad (11)$$

where $\hat{R}'$ is the total number of symbols without the formation of the candidate sequence and $r_j$ is the frequency of the jth symbol in the candidate sequence.

Model costs require a method for not only spelling out the candidate sequence but also the cost of encoding the length of the sequence to be described. This cost is estimated as:

$$C_m = M(l_i) + \sum_{j=1}^{l_i} \log\left(\frac{\hat{R}'}{r_j}\right) \quad (12)$$

where M(L) is the shortest prefix-encoding for the length sequence.

In this way both a practical method for spelling out the model for implementation and an online method for determining model costs that relies only on known information is achieved. Since new symbols will add to the cost of other symbols simply by increasing the number of symbols in the alphabet, an additional cost is specified that reflects the change in costs of subsequences that are not covered by candidate sequences. The effect is estimated by:

$$C_o = (\hat{R} - R_i) \cdot \log\left(\frac{L+2}{L+1}\right). \quad (13)$$

This provides an accurate SCR heuristic as follows:

$$SCR = \frac{C_m + C_h + C_o}{C_p}. \quad (14)$$

In addition to or instead of the SCR heuristic, other heuristics may be employed in accordance with the present technique. For example, two alternative heuristics include the longest match (LM) heuristic and the total compression (TC) heuristic. Both of these heuristics leverage the gains described above by considering the entropy of specific variables and terminals when selecting candidate sequences. For example, the LM heuristic selects the longest sequence for substitution, even if only repeated once. This heuristic may be useful when it is anticipated that the importance of a codeword is proportional to its length. The present technique may apply LM to greater advantage than other compression techniques because of its deep recursion so that, when a long sequence is added to the codebook, the subsequences comprising that sequence, rather than being disqualified, remain potential candidates for subsequent sequences. For example, if the longest sequence merely repeats the second-longest sequence three times, the present technique will identify both sequences.

When the TC heuristic is applied, the sequence that leads to maximum compression at the current iteration is chosen. This process does not necessarily increase the SCR, and may lead to the elimination of smaller sequences from the codebook. In one embodiment, this approach may be tempered by including the model in the search space of future iterations. Because of this deep recursion, subsequences in both the model and data portions of a sequence are considered as candidate sequences at each iteration. As with all MDL criteria, the best heuristic, or sequential combination of heuristics, for a given sequence is the approach that best compresses the data. Thus, the TC gain is the improvement in compression achieved by selecting a candidate sequence and may be derived from the SCR heuristic by removing the normalization factor.

Figure 4:
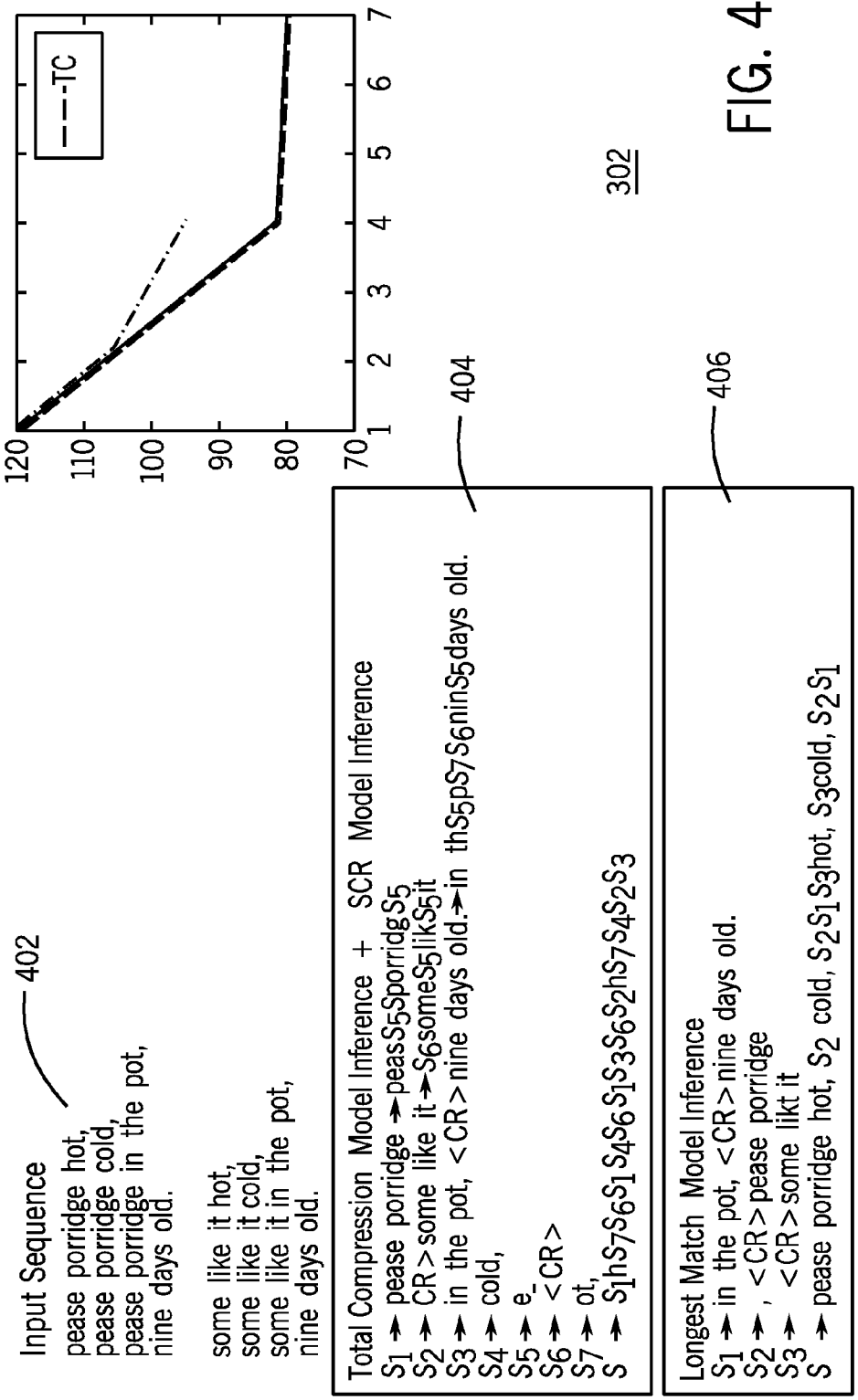
FIG. 4 illustrates the calculation of, and output, of compression descriptors in accordance with one aspect of the present technique.

FIG. 4 illustrates the calculation of, and output, of descriptors in accordance with one aspect of the present technique. In this example, an input sequence 402 is compressed via multiple heuristics and the results of TC and SCR compression are shown at 404, while the results of LM compression are shown at 406.

Both the TC and SCR heuristics 404 achieve the same total compression and both exceed the performance of the LM heuristic 406 in this example.

After the model has been created, such as by the heuristics described above, additional possibilities for compression may still exist. For example, regions of local similarity may provide an opportunity for additional compression to the extent that a sequence may be defined as a concatenation of multiple shorter and adjacent sequences already in the grammar. Likewise, in the context of DNA or RNA analysis, single nucleotide polymorphisms (SNPs) may allow a sequence to be defined as a single nucleotide alteration to another sequence already in the grammar. In a non-DNA or RNA context, such an approach might be equated with treating a misspelled word or single character difference as an already identified sequence, such as equating "A_rose" or "a_rowe" with "a_rose" in the preceding examples.

Further, a priori information may be incorporated into the model inference algorithm leading to improved compression performance where such information is available, such as where the data series 104 is a DNA or RNA sequence. For example, in the DNA context, information may be available relating to the types of structures that are typical of naturally occurring DNA sequences. This prior information may then be incorporated into the model inference algorithm. Likewise, the search for, and grammar encoding of, reverse-complement matches in DNA and RNA analyses is readily implemented by adding the reverse-complement of a sequence to the new model and taking account of the frequency of the sequence and its reverse-complement in motif identification.

The various approaches to the analysis of a data series 104 provided herein may be used to identify sequences (such as due to their repetitiveness and length) in the data series 104 that that merit further research. For example, the MDL techniques described herein may be used to identify micro RNA (miRNA) target sites in disease-related genes. In such an approach, mRNA transcripts may be analyzed as described herein to identify short sequences that are repeated and localized to the 3' UTR. Comparative genomics may be applied to check that MDL sequences in fact represent candidate miRNA target sites, even if there are no known cognate miRNAs that will bind to that site.

The present technique was employed to identify the miRNA binding site in the 3'UTR of the tumor suppressor gene, LATS2. A function-based approach to miRNA target site identification, determined that LATS2 is regulated by miRNAs 372 and 373. Increased expression of these miRNAs led to down-regulation of LATS2 and to tumorigenesis. The miRNA 372 and 373 target sequence (AGCACTTATT) (SEQ ID NO 1) is located in the 3'UTR of LATS2 mRNA and is repeated twice but was not previously identified with computation-based miRNA target identification techniques. In accordance with the present technique, using the 3'UTR of LATS2 mRNA as an input data series, three sequences were identified using longest match (LM) mode: the polyA tail, the miRNA 372 and 373 target sequence (AGCACTTATT) (SEQ ID NO 1), and a third sequence (AAACAGGAC) that has not been identified with any particular biological function at this time. This demonstrates that analyzing genes of interest a priori in accordance with the present techniques produces highly relevant sequence motifs.

Since miRNAs regulate genes implicated in tumorigenesis and the new program is able to identify these targets, the present techniques may be used to directly identify genes that are important for tumorigenesis. This was tested by using a target-rich set of 144 genes known to have increased expression patterns in ErbB2-positive breast cancer. The mRNA sequence of each gene was compressed, as described herein, using the LM approach. A total of 93 sequences were identified as resulting in compression of these genes. Of these sequences, 25 were found exclusively in the 3'UTRs of these genes.

The 25 3'UTR sequences identified were searched to determine their level of conservation in the human and other genomes and to determine possible sequence similarities to known miRNAs. One identified sequence was found to be highly conserved, resulted in matches to a small number of miRNAs that fulfill the minimum requirements of putative miRNA targets, and was implicated by in vitro data in breast cancer progression. These results demonstrate the potential for use of the present techniques in identifying sequences of biological interest or of identifying other sequences of interest in other data analysis contexts.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for identifying a sequence of interest in a data series, comprising:
   generating a data structure that stores characteristics about a plurality of sequences present in the data series;
   identifying one or more sequences based upon the contents of the data structure;
   evaluating one or more exit criteria to determine if an exit point has been reached;
   updating the data structure to reflect the most recent identification of a sequence and
   repeating the identification process if the exit criteria are not met; and
   terminating if the exit criteria are met.

2. The method recited in claim 1, comprising providing at least one identified sequence to a user upon termination.

3. The method recited in claim 1, wherein the data structure is generated by analyzing the data series only once.

4. The method recited in claim 1, wherein the data structure is iteratively updated and maintained as sequence identification proceeds, without further reference to the data series.

5. The method recited in claim 1, wherein the data series comprises at least one of numerals, letters, or punctuation marks.

6. The method recited in claim 1, wherein the data series is a biological sequence selected from a deoxyribonucleic acid (DNA) sequence, a ribonucleic acid (RNA) sequence, or a peptide sequence.

7. A method for identifying a sequence of interest, comprising:
   evaluating a plurality of heuristics for a candidate sequence from a plurality of candidate sequences present in a data series;
   identifying a sequence in the plurality of candidate sequences based on the evaluation of the heuristics;
   evaluating one or more exit criteria to determine if an exit point has been reached;
   updating the data series or a corresponding data structure to reflect the most recent identification of a sequence and repeating the steps of evaluating the plurality of heuristics and identifing the sequences if the exit criteria are not met; and
   terminating if the exit criteria are met.

8. The method recited in claim 7, comprising providing at least one identified sequence to a user upon termination.

9. The method recited in claim 7, wherein each heuristic comprises a data compression heuristic.

10. The method recited in claim 7 comprising calculating the plurality of heuristics for each respective candidate sequence.

11. The method of claim 7, wherein the plurality of heuristics are calculated using minimum description length (MDL) principles.

12. The method of claim 7, wherein the plurality of heuristics comprise different heuristic permutations derived for more than one iteration.

13. The method of claim 7, wherein at least one of the plurality of heurisitics comprises a symbol compression ratio (SCR) heuristic, a longest match (LM) heuristic, or a total compression (TC) heuristic.

14. A method for identifying a biological sequence of interest, comprising:
   generating a data structure that stores characteristics about potential biological sequences of interest present in a biological polymer;
   identifying one or more biological sequences based upon the contents of the data structure;
   evaluating one or more exit criteria to determine if an exit point has been reached;
   updating the data structure to reflect the most recent identification of a biological sequence and
   repeating the identification process if the exit criteria are not met; and
   terminating if the exit criteria are met.

15. The method recited in claim 14, comprising providing at least one identified biological sequence to a user upon termination.

16. The method recited in claim 14, wherein the biological polymer comprises one of a deoxyribonucleic acid (DNA) sequence, a ribonucleic acid (RNA) sequence, or a peptide sequence.

17. The method recited in claim 14, wherein the data structure is generated by analyzing the biological polymer only once.

18. The method recited in claim 14, wherein the data structure is iteratively updated and maintained, without further reference to the biological polymer.

19. One or more tangible, machine-readable media, comprising:
   code adapted to generate a data structure that stores characteristics about a plurality of sequences present in a data series;

code adapted to identify one or more sequences based upon the contents of the data structure;

code adapted to evaluate one or more exit criteria to determine if an exit point has been reached;

code adapted to update the data structure to reflect the most recent identification of a sequence and repeating the identification process if the exit criteria are not met; and code adapted to terminate if the exit criteria are met.

20. The tangible, machine-readable media recited in claim 19, wherein the code is adapted to provide at least one identified sequence to a user upon termination.

21. The tangible, machine-readable media recited in claim 19, wherein the code adapted to generate the data structure generates at least one of a matrix structure or a sequence array.

22. The tangible machine-readable media recited in claim 19, wherein the code adapted to generate the data structure analyzes the data series only once.

23. The tangible, machine-readable media recited in claim 19, wherein the code adapted to update the data structure iteratively updates the data structure without further reference to the data series.

24. One or more tangible, machine-readable media, comprising:

code adapted to evaluate a plurality of heuristics for a candidate sequence from a plurality of candidate sequences present in a data series;

code adapted to identify a sequence in the plurality of candidate sequences based on the evaluation of the heuristics;

code adapted to evaluate one or more exit criteria to determine if an exit point has been reached;

code adapted to update the data series or a corresponding data structure to reflect the most recent identification of a sequence and repeating the steps of evaluating the plurality of heuristics and identifing the sequences if the exit criteria are not met; and code adapted to terminate if the exit criteria are met.

25. The tangible, machine-readable media recited in claim 24, comprising code adapted to provide at least one identified sequence to a user upon termination.

26. The tangible, machine-readable media recited in claim 24, wherein each heuristic comprises a data compression heuristic.

27. The tangible, machine-readable media recited in claim 24 comprising code adapted to calculate the plurality of heuristics for each respective candidate sequence.

28. The tangible, machine-readable media of claim 24, wherein the plurality of heuristics are calculated using minimum description length (MDL) principles.

29. The tangible, machine-readable media of claim 24, wherein the plurality of heuristics comprise different heuristic permutations derived for more than one iteration.

30. The tangible, machine-readable media of claim 24, wherein at least one of the plurlaity of heurisitics comprises a symbol compression ratio (SCR) heuristic, a longest match (LM) heuristic, or a total compression (TC) heuristic.

* * * * *

UNITED STATES PATENT AND TRADEMARK OFFICE
CERTIFICATE OF CORRECTION

| | | |
|---|---|---|
| PATENT NO. | : 7,809,765 B2 | Page 1 of 1 |
| APPLICATION NO. | : 11/844619 | |
| DATED | : October 5, 2010 | |
| INVENTOR(S) | : Evans et al. | |

It is certified that error appears in the above-identified patent and that said Letters Patent is hereby corrected as shown below:

Title Page, Item (56), under "OTHER PUBLICATIONS", in Column 2, Line 5, after "Complexity",", insert -- 2001CRD159, Class 1, --.

In Column 5, Line 14, delete "$I_{avg}$," and insert -- $l_{avg}$, --, therefor.

In Column 6, Lines 55-56, in Equation (2), delete "$K_\phi(x) \stackrel{+}{=} \{K(S) + \log_2 |S|\}$," and insert -- $K_\varphi(x) \stackrel{+}{=} \{K(S) + \log_2 |S|\}$ --, therefor.

In Column 7, Line 11, delete "$\stackrel{+}{=}, \stackrel{+}{=} defines$," and insert -- $\stackrel{+}{h}. \stackrel{+}{h} defines$ --, therefor.

In Column 13, Line 65, in Claim 7, delete "identifing" and insert -- identifying --, therefor.

In Column 14, Line 32, in Claim 13, delete "heurisitics" and insert -- heuristics --, therefor.

In Column 16, Line 6, in Claim 24, delete "identifing" and insert -- identifying --, therefor.

In Column 16, Line 25, in Claim 30, delete "plurlaity of heurisitics" and insert -- plurality of heuristics --, therefor.

Signed and Sealed this
Twenty-eighth Day of February, 2012

David J. Kappos
*Director of the United States Patent and Trademark Office*